United States Patent [19]

Krauss

[11] 4,410,701
[45] Oct. 18, 1983

[54] PROCESS FOR MAKING PYRIDYLOXYPHENOL COMPOUNDS

[75] Inventor: Richard C. Krauss, Midland, Mich.

[73] Assignee: The Dow Chemical Company, Midland, Mich.

[21] Appl. No.: 373,386

[22] Filed: Apr. 30, 1982

Related U.S. Application Data

[63] Continuation-in-part of Ser. No. 269,300, Jun. 1, 1981, abandoned.

[51] Int. Cl.³ ........................................... C07D 213/64
[52] U.S. Cl. .................................................... 546/302
[58] Field of Search ....................................... 546/302

[56] References Cited

U.S. PATENT DOCUMENTS 4,046,553 9/1977 Takahashi et al. ..................... 71/94
4,152,328 5/1979 Nishiyama et al. ................. 546/302
4,275,212 6/1981 Orvik .................................. 546/290

Primary Examiner—Alan L. Rotman

[57] ABSTRACT

Process for making pyridyloxyphenol by reacting under essentially anhydrous conditions in the absence of oxygen and in a polar aprotic solvent, a 2-halopyridine with hydroquinone which has been from 75 to 100 percent neutralized to the sodium or potassium salt.

7 Claims, No Drawings

PROCESS FOR MAKING PYRIDYLOXYPHENOL COMPOUNDS

CROSS REFERENCE TO RELATED APPLICATIONS

This application is a continuation-in-part of Ser. No. 269,300 filed June 1, 1981, abandoned.

BACKGROUND OF THE INVENTION

Pyridyloxyphenol compounds may be prepared by the reaction of a 2-substituted pyridine compound with a hydroquinone and an alkaline material, as taught in U.S. Pat. No. 4,046,553 issued Sept. 6, 1977 and in U.S. Pat. No. 4,275,212 issued June 23, 1981. In these reactions, the products of side reactions, such as hydrolysis, often constitute 5 or more weight percent of the obtained material. They may also be prepared by reacting appropriate diethers with a dihydroxybenzene in a polar aprotic solvent in the presence of 0.1 to 1 mole of alkali per mole of diether as taught in U.S. Pat. No. 4,214,086 issued July 22, 1980. This reference also teaches that, if desired, a further solvent which forms an azeotrope with water, may be employed.

SUMMARY OF THE INVENTION

This invention provides a process for making pyridyloxyphenol compounds by reacting a 2-substituted pyridine compound with a hydroquinone and an alkaline material under essentially anhydrous conditions. More particularly, the invention provides a process for making pyridyloxyphenol compounds having the formula

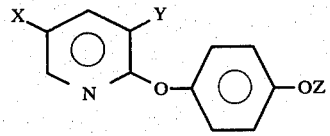

wherein X is chloro or trifluoromethyl, Y is hydrogen or chloro and Z is hydrogen, sodium or potassium, which comprises dissolving hydroquinone in a polar aprotic solvent, heating under vacuum to degas, adding sufficient aqueous sodium or potassium hydroxide to neutralize from 75 to 100 percent of the hydroquinone, while continuing to heat under vacuum to distill off the water until less than 1 weight percent water, based on total weight of solvent and reactants, remains, releasing the vacuum with a dry inert gas, cooling and adding a 2-halopyridine having the formula

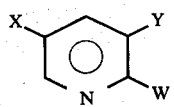

wherein X and Y are as above defined and W is bromo, chloro, fluoro or iodo.

DETAILED DESCRIPTION OF THE INVENTION

In carrying out the process of this invention, the selected pyridine and hydroquinone reactants are contacted in the absence of oxygen, i.e., under an inert atmosphere, e.g., nitrogen, helium or argon, in the presence of an inert carrier medium, i.e., a polar aprotic solvent such as, for example, dimethylsulfoxide (DMSO), dimethylformamide, diethylacetamide or N-methylpyrrolidone under essentially anhydrous conditions to provide the desired pyridyloxyphenol compounds in higher yields and purity than prior art methods, i.e., the products of side reactions such as hydrolysis often constitute less than 1 percent and advantageously less than 0.5 percent of the obtained material.

To obtain the desired anhydrous conditions the hydroquinone reactant is, typically, dissolved in the polar aprotic solvent, the solution heated under vacuum (advantageously about 100° C. at 100 mm Hg) to degas, the desired amount of aqueous caustic is added while continuing to heat under vacuum and water is removed by distillation. When all of the water is removed, i.e., less than 1 weight percent and, preferably, less than 0.5 weight percent (based on total weight of the mixture) of water remains, the vacuum is released with dry inert gas, e.g., nitrogen, the slurry of disodium or dipotassium hydroquinone is cooled and the desired pyridine compound is added. This latter reaction may be carried out at temperatures of from 25° to 150° C., but is preferably carried out at 70° to 100° C.

The amount of sodium or potassium hydroxide required is that amount necessary to neutralize from 75 to 100 percent, advantageously 90 to 100 percent, of the hydroquinone reactant.

The invention is further illustrated by the following examples in which all stated percentages are weight percents unless otherwise indicated:

EXAMPLE 1

A solution of 22.5 g (0.205 mole) of hydroquinone in 200 ml of DMSO was heated to 100° C. under vacuum (100 mm Hg) to degas and 31.5 g (0.394 mole) of 50 percent aqueous NaOH were added over 10 minutes while continuing to heat the solution at 100 mm pressure. Water began to distill and was removed through a five-plate Oldershaw Column operated with reflux. The pot temperature rose gradually to 128° C. while the head temperature remained constant at about 55° C. After about 35 ml of distillate had been collected, the head temperature rose rapidly to 125° C. The distillation was continued until about 80 ml had been collected. The vacuum was released with dry N₂, the slurry of disodium hydroquinone was cooled to 70° C. and 43.2 g (0.2 mole) of 2,3-dichloro-5-(trifluoromethyl) pyridine were added over about 5 minutes. The reaction exothermed and cooling was initially required to maintain the temperature below 80° C. for 30 minutes. The reaction was held at 80° C. At this time, analysis by high pressure liquid chromatography (HPLC) showed the product compensation to be:

-continued

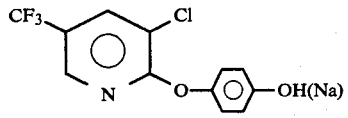
~99 wt. %

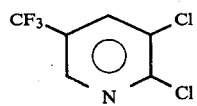
none detected

EXAMPLE 2

A solution of 22. 5 g (0.205 mole) of hydroquinone in 200 ml of DMSO was heated to boiling under a five-plate Oldershaw Column at 100 mm Hg pressure and 25.5 g (0.454 mole) of KOH in 25 ml water were added dropwise over three hours while continuously distilling off water. After addition was complete, the distillation was continued to a pot temperature of 128° C. and head temperature of 123° C. The total distillate was 110 ml. The vacuum was released with dry nitrogen, the slurry cooled to 70° C. and 43.2 g (0.2 mole) of 2,3-dichloro-5-(trifluoromethyl)pyridine were added dropwise over 10 minutes. The reaction was held at 80° C. for 90 minutes. HPLC analysis showed the desired product with only 1.1 weight percent of

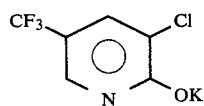

and 0.5 percent of the bis compound.

EXAMPLE 3

A solution of 22.5 g (0.205 mole) of hydroquinone in 300 ml N-methylpyrrolidone was heated to boiling at 20 mm Hg pressure under a 10-plate Oldershaw Column, 31.5 g (0.394 mole) of 50 percent aqueous sodium hydroxide were added dropwise over 20 minutes and water was distilled off. The total distillate was 50 ml. The vacuum was released with dry nitrogen, the slurry cooled to 80° C. and 43.2 g (0.2 mole) of 2,3-dichloro-5-(trifluoromethyl)pyridine were added all at once. The reaction mixture exothermed about 10° C. and was further heated to 100° C. and held one hour to give the desired product containing only 1.4 weight percent of

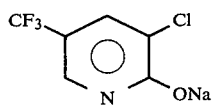

and 0.25 weight percent of the bis compound.

EXAMPLE 4

A solution of 11.3 g (0.103 mole) of hydroquinone in 145 ml DMSO was heated to boiling under a 10-plate Oldershaw Column at 100 mm Hg pressure, 15.6 g (0.195 mole) of 50 percent aqueous sodium hydroxide were added dropwise over two minutes and water was distilled off. The total distillate was 60 ml. The vacuum was released with dry nitrogen, the slurry cooled to 70° C. and 18.1 g (0.1 mole) of 2-chloro-5-(trifluoromethyl)-pyridine were added all at once. The reaction exothermed to 100° C. and was held there for 30 minutes to give sodium 4-(5-(trifluoromethyl)-2-pyridyloxy)phenate containing less than 1 weight percent of

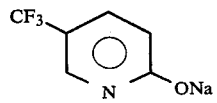

and 0.5 weight percent of the bis compound.

EXAMPLE 5

Following the procedure of Example 4 a slurry of 0.1 mole hydroquinone disodium salt was prepared and 21.6 g (0.1 mole) of 2,3-dichloro-5-(trifluoromethyl)-pyridine was added at 110° C. The reaction exothermed and was held at 130° to 135° C. for five minutes to give the desired product containing only 0.3 weight percent of

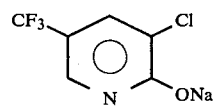

and 0.1 weight percent of the bis compound.

Various modifications may be made in the present invention without departing from the spirit or scope thereof and it is understood that I limit myself only as defined in the appended claims.

I claim:

1. Process for making pyridyloxyphenol compounds having the formula

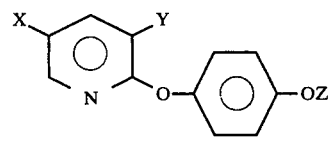

wherein X is chloro or trifluoromethyl, Y is hydrogen or chloro and Z is hydrogen, sodium or potassium, which consists essentially of dissolving hydroquinone in a polar aprotic solvent, heating under vacuum to degas, adding sufficient aqueous sodium or potassium hydroxide to neutralize from 75 to 100 percent of the hydroquinone, while continuing to heat under vacuum to distill off the water until less than 1 weight percent water, based on total weight of solvent and reactants, remains, releasing the vacuum with a dry inert gas, cooling and adding a 2-halopyridine having the formula

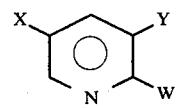

wherein X and Y are as above defined and W is bromo, chloro, fluoro or iodo, and heating whereby the said halopyridine reacts with the neutralized and dried hydroquinone, producing the desired mono- or disubstituted-2-pyridyloxy phenolic derivative wherein the reaction is carried out at a temperature of from 25° to 150° C.

2. Process of claim 1 wherein the reaction temperature is from 70° to 100° C.

3. Process of claim 1 wherein the 2-chloropyridine copound is 2,3-dichloro-5-(trifluoromethyl)pyridine.

4. Process of claim 1 wherein the 2-chloropyridine compound is 2-chloro-5-(trifluoromethyl)pyridine.

5. Process of claim 1 wherein the solvent is dimethylsulfoxide.

6. Process of claim 1 wherein the solvent is N-methyl pyrrolidone.

7. Process of claim 1 wherein the hydroquinone has been from 90 to 100 percent neutralized to the sodium salt.

* * * * *

UNITED STATES PATENT AND TRADEMARK OFFICE
CERTIFICATE OF CORRECTION

PATENT NO. : 4,410,701
DATED : October 18, 1983
INVENTOR(S) : Richard C. Krauss

It is certified that error appears in the above—identified patent and that said Letters Patent is hereby corrected as shown below:

Col. 2, line 54, "compensation" should read --composition--.

Col. 5, line 4, "copound" should read --compound--.

Signed and Sealed this

Seventh Day of February 1984

[SEAL]

Attest:

GERALD J. MOSSINGHOFF

Attesting Officer     Commissioner of Patents and Trademarks